United States Patent [19]

Donachy et al.

[11] Patent Number: 5,260,272

[45] Date of Patent: Nov. 9, 1993

[54] POLYANIONIC POLYAMINO ACID INHIBITORS OF MINERAL DEPOSITION AND THEIR SYNTHESIS

[75] Inventors: Julie Donachy; Steven Sikes, both of Mobile, Ala.

[73] Assignee: University of South Alabama, Mobile, Ala.

[21] Appl. No.: 677,332

[22] Filed: Mar. 29, 1991

[51] Int. Cl.$^5$ .......................... C02F 5/10; C07C 7/06; C07C 7/08; C07C 7/10
[52] U.S. Cl. ........................................ 524/12; 514/13; 514/14; 514/15; 514/16; 514/17; 514/824; 514/501; 424/49; 424/54; 427/384; 433/215; 530/333
[58] Field of Search .................... 514/12–17, 514/824, 901; 530/324–330, 333; 427/384; 429/49, 54; 433/215

[56] References Cited

U.S. PATENT DOCUMENTS

| | | | |
|---|---|---|---|
| 4,866,161 | 9/1989 | Sikes et al. | 530/324 |
| 4,868,287 | 9/1989 | Sikes et al. | 530/324 |
| 5,051,401 | 9/1991 | Sikes | 514/12 |

Primary Examiner—Lester L. Lee
Attorney, Agent, or Firm—Oblon, Spivak, McClellland, Maier & Neustadt

[57] ABSTRACT

Polypeptides of the formula $$\text{poly } (X)_m (Y)_n,$$

wherein
X is selected from the group consisting of aspartate, glutamate, glutamine, asparagine, mixtures and block polymers thereof,
Y is selected from the group consisting of phosphoserine, sulfoserine, phosphohomoserine, phosphotyrosine, phosphothreonine, phosphoglutamine, phosphoasparagine, serine, alanine, dehydroalanine and mixtures thereof,
$m = 5-199$ and
$n = 1-10$ have been demonstrated to inhibit mineral deposition, and can be employed in the inhibition of mineral deposition in both in vitro and in vivo applications. Serine-containing polypeptides can be thermally synthesized by combining the necessary amino acid residues in a reaction vessel, eliminating oxygen to preclude charring, and heating said reaction vessel in a heating medium to a temperature of about 155° C.

15 Claims, 2 Drawing Sheets

POLYANIONIC POLYAMINO ACID INHIBITORS OF MINERAL DEPOSITION AND THEIR SYNTHESIS

BACKGROUND OF THE INVENTION

This invention relates to the discovery of new polyamino acids and their synthesis. The polyamino acids are powerful inhibitors of mineral formation, particularly the crystallization of calcium carbonate and calcium phosphate. The molecules may be useful in a variety of applications including but not limited to tartar control, prevention of industrial scaling, use as dispersants, corrosion inhibition, prevention of pathological calcification, and control of biofouling.

DISCUSSION OF BACKGROUND

Biological mineralization is a fundamental process in nature. Unfortunately mineral deposits frequently occur where they are not wanted. In the body, mineral deposition may contribute to dental plaque, hardening of the arteries, various organ stones and the failure of prosthetic devices like implanted heart valves. In the marine environment, the biomineral structures may cause problems as in the case of barnacles growing on the hulls of ships, adding extra bulk and creating drag. In industry, mineral scale forms on surfaces of cooling towers and other devices preventing their proper operation as heat exchangers and frequently promoting localized corrosion.

Because of the problems associated with unwanted mineral deposition, much effort has been devoted to finding mineralization inhibitors, particularly in industry, that might be used to prevent harmful mineral formation.

Among the newest approaches to developing mineral deposition inhibitors is the study of naturally-occurring proteins and polysaccharides that regulate mineral formation by organisms (Sikes, C. S. and A. P. Wheeler (1985). Inhibition of inorganic or biological $CaCO_3$ deposition by polyamino acid derivatives. U.S. Pat. No. 4,534,881; Sikes, C. S. and A. P. Wheeler (1986). Inhibition of inorganic and biological $CaCO_3$ deposition by a polysaccharide fraction obtained from $CaCO_3$— forming organisms. U.S. Pat. No. 4,585,560; Wheeler, A. P. and C. S. Sikes (1986). Inhibition of the formation of inorganic or biological $CaCO_3$-containing deposits by a proteinaceous fraction obtained from $CaCO_3$-forming organisms. U.S. Pat. No. 4,587,021). This approach led to the identification of a new class of polyanionic/hydrophobic peptides (Sikes, C. S. and A. P. Wheeler (1989). Inhibition of mineral deposition by polyanionic/hydrophobic peptides and derivatives thereof having a clustered block copolymer structure. U.S. Pat. No. 4,868,287) and phosphorylated and related polyanionic peptides (Sikes, C. S. Inhibition of mineral deposition by phosphorylated and related polyanionic peptides. U.S. patent application No. 07/339,672) that are even more powerful inhibitors of crystallization on a weight basis than the natural proteins. The preferred structure of the phosphopeptides is identified as $Asp_{(x)}PSer_{(y)}$ with $x=10$ to $40$ and $y=1$ to $3$.

Solid phase synthesis techniques described to make these peptides are presently thought to be commercially non-viable due to the costs involved. Now the inventors have discovered new polyamino acids, including a cost effective method for their bulk synthesis.

Clues for development of this method were taken from the observation that mixtures of $\alpha$-amino acids could be thermally polymerized into proteinoids (Fox, S. W. and K. Harada (1958). Thermal copolymerization of amino acids to a product resembling protein. *Science*, 128, 1214; Fox, S. W. and K. Harada (1959). The thermal copolymerization of amino acids common to protein. *J. Am. Chem. Soc.*, 82, 3745-3751) at temperatures above 150° C. The synthesis required the presence of excess dicarboxylic amino acids for unknown reasons. It was further noted that there was a high reproducibility in the copolymerization of amino acids (Fox, S. W. and C. R. Windsor (1984). Reproducibility of amino acid compositions in repeated copolymerizations of amino acids. *Int. J. Quart. Biol. Symp.*, 11, 103-108). This suggested a possible simple method for preparing mineral deposition inhibitors which are composed primarily of the dicarboxylic amino acid aspartate.

However, the advantage of excess dicarboxylic amino acid was reportedly lost above 210° C., with thermal decomposition of the amino acids. A further problem was that incorporation of serine into proteinoid was generally not possible due to thermal decomposition even at relatively low temperatures. When serine was incorporated to a limited extent under mild conditions, yields were quite low (Fox, S. W. and K. Harada (1960). Thermal copolymerization of amino acids common to protein. *J. Am. Chem. Soc.*, 87, 3745-3751; Fox, S .W., K. Harada and D. L. Rohlfing (1962). The thermal copolymerization of $\alpha$-amino acids, in: M. A. Stahmann (ed.), Polyamino Acids, Polypeptides, and Proteins. Univ. of Wisconsin Press, Madison, pp. 47-54).

The inventors now report methods of increasing the incorporation of serine into thermal polyamino acids. The effects of varying the composition and ratios of reactants, solvent systems, temperature, and time of synthesis were examined.

In short, the present invention identifies new polyanionic polypeptide molecules and a method of synthesis. The molecules preferably contain a polyaspartate backbone with phosphoserine or a derivative thereof incorporated into the polymer. Sulfated, phosphonated and sulfonated derivatives of serine and other amino acids are also contemplated for incorporation into the aspartate backbone. Such polypeptides of this invention and the method of synthesis have not been specifically described before. Additionally, the method of synthesis has not been described previously with the exception of thermal polyaspartic acid.

SUMMARY OF THE INVENTION

Accordingly, it is an objective of the present invention to provide new and improved materials for inhibiting mineral deposition.

It is another objective of this invention to provide a method for bulk synthesis of these materials.

It is another objective of the present invention to provide materials for prevention of formation of calculus or plaque on teeth.

It is another objective of the present invention to provide materials that can prevent mineralization in a marine environment, such as by prevention of barnacle accumulation.

It is another objective of the present invention to provide materials that can effectively prevent mineralization of prosthetic devices implanted in the body.

It is another objective of the present invention to provide materials for prevention of mineralization in arteries associated with arteriosclerosis, or atherosclerosis.

It is another objective of the present invention to provide materials that can prevent mineralization in an industrial setting, such as scaling in cooling towers and boilers.

It is another objective of the present invention to provide for materials that can prevent corrosion of metallic surfaces.

These and other objectives of the present invention which will hereinafter become more readily apparent have been accomplished by providing new polypeptide materials that have the following general formula. The materials consist of a block of anionic amino acids connected to another block that contains anionic derivatives of hydroxylated or aminated amino acids mixed with hydrophobic residues.

$$poly(X)_m(Y)_n$$

where each X is aspartate, glutamate, glutamine, asparagine, or anionic derivatives of these amino acids or a block polymer thereof.

each Y is an anionically derived amino acid such as phosphoserine, sulfoserine, phosphohomoserine, phosphotyrosine, phosphothreonine, phosphoglutamine, phosphoasparagine or mixtures of these residues; serine; alanine, or dehydroalanine.

$m = 5$ to $199$ $n = 1$ to $40$

It should be noted that occasional random monomers may appear in a short sequence, or between blocks, but the molecule is substantially characterized as a block copolymer.

These polypeptides may be prepared by thermal polymerization of, e.g., polyaspartic acid, aspartic acid and serine. The selected amino acids are placed in a reaction container, such as an Erlenmeyer flask. The reaction vessel is partially submerged in a heating medium, such as cooking oil, and heated to a temperature below the decomposition temperature of serine. An effective reaction temperature is 155° C.±2° C. Oxygen is eliminated from the reaction vessel to preclude charring by, e.g., continuously purging the reaction vessel with a stream of nitrogen. The reaction may be continued for up to 24 hours. If necessary, the product is purified by dissolving it in distilled water, and dialyzing it against the same to remove any unreacted amino acids. For some polypeptides, to achieve sufficient size, a starting backbone of thermally polymerized polyaspartate is required. Pre-existing polyaspartate can be introduced into the reaction vessel with serine, the pre-existing polyaspartate being prepared by separate temperature synthesis, either low or high temperature. In low temperature synthesis, aspartic acid is placed in a reaction vessel entrained in a heating medium such as cooking oil at about 190° C. Oxygen is purged, using a stream of nitrogen, to preclude charring. The reaction process may continue up to 72 hours. In high temperature synthesis, the aspartic acid is placed in a baking dish, and heated at 240° C. in a muffle oven for up to 8 hours. Nearly 100% of the aspartic acid polymerized, requiring no further purification. High temperature thermally synthesized polyaspartate exhibits greater activity when compared to low temperature thermally synthesized polyaspartate, as an inhibitor of mineral formation.

The present invention is also directed to compositions containing these materials, such as dentifrices and mouthwashes for oral application.

DETAILED DESCRIPTION OF THE PREFERRED EMBODIMENTS

Figure 1:
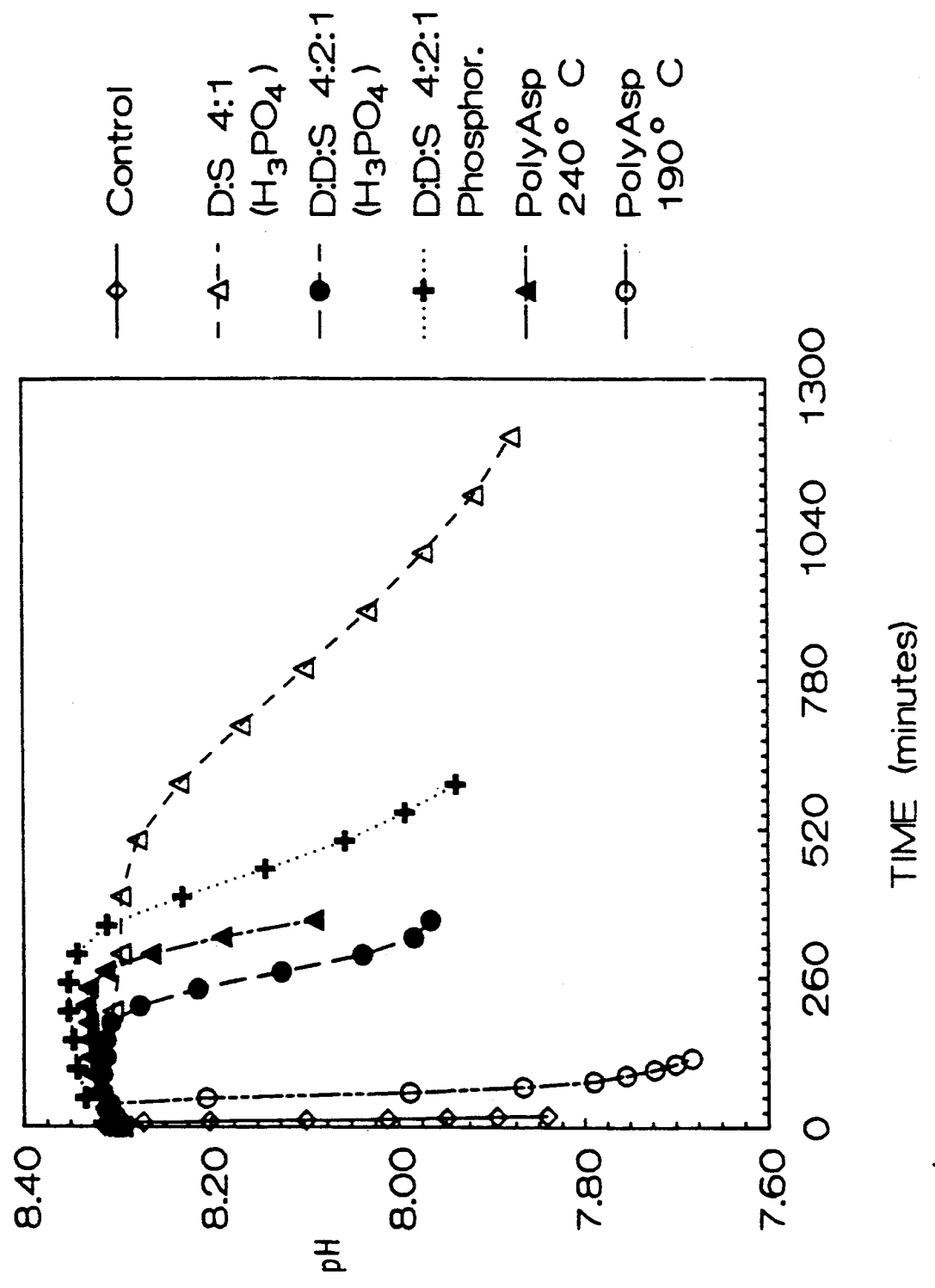
FIG. 1. Calcium carbonate pH-drift assay. Peptide does is 0.05 µg/ml. D=Asp; S=Ser.

In a preferred embodiment X is aspartate or glutamate, particularly preferably aspartate and most preferably polyaspartate of 10 to 60 amino acid residues.

The preferred amino acid composition of one peptide is 1 to 10 phosphoserines most preferably 3 to 6 with oither derivatives of serine comprising approximately 2 to 5 residues of the molecule. The remainder of the polypeptide is aspartic acid preferably present as a block polymer of 40 to 60 residues.

The preferred amino acid composition of another peptide is 1 to 10 residues of alanine which result from serine decomposition; 1 to 12 residues of other derivatives of serine such as dehydroalanine most preferably 3 to 6; 0 to 2 residues of serine and the remainder polyaspartic acid most preferably as a block polymer of 40 to 60 residues.

The preferred amino acid composition of another peptide is between 2 and 10 residues of derivatives of serine such as alanine and dehydroalanine most preferably 5 to 7 and the remainder of the peptide is 20 to 40 residues of aspartic acid.

Methods of Synthesis

This invention relates to methods of synthesis of the above described polypeptides. As solid phase methods previously described for the synthesis of mineral deposition inhibitors (Sikes, C. S. Inhibition of mineral deposition by phosphorylated and related polyanionic peptides. U.S. patent application No. 07/339,672) are expensive, cost effective methods for bulk synthesis were developed. Peptides of desired sequence and size may be made by thermal polymerization of amino acids.

For example a mixture of thermally polymerized polyaspartic acid, aspartic acid, and serine were placed in an Erlenmeyer flask. The reaction vessel was partially submerged in cooking oil heated to 155° C. (±2° C.). A stream of nitrogen was continuously purged into the reaction vessel to eliminate $O_2$ and the possibility of charring. The reaction was allowed to continue for up to 24 hours. The product is purified by dissolving it in distilled water and dialyzing it against the same to remove any unreacted amino acids.

DETAILED DESCRIPTION OF PREFERRED METHODS

For some polypeptides a starting backbone of thermal polyaspartate is required to provide sufficient size of the final product, given the relatively low reaction temperatures. Temperatures above 170° C. led to decomposition of serine. Even at 155° C., an excess of free aspartic acid was required for the serine to survive. Under these specific conditions, which were heretofore undescribed in the art, enough serine molecules become incorporated into the preexisting polyaspartate to produce the molecules of the invention. The polyaspartate backbone can be prepared in one of two ways as detailed below.

Low Temperature Synthesis of Polyaspartate:

This method is described in Sikes, C. S. Inhibition of mineral deposition by phosphorylated and related polyanionic peptides. U.S. patent application No. 07/339,672. The entire disclosure of this application is incorporated herein by reference.

L-aspartic acid (500 g) was placed in a two-liter, round-bottom reaction vessel. The reaction vessel was partially submerged in cooking oil at 190° C. ($\pm 2°$ C.). The reaction vessel was coupled by ground glass fitting to a condenser vessel, which in turn was fitted to a rotator shaft driven by a rheostated electric motor. A stream of nitrogen was continuously purged into the condenser vessel to eliminate $O_2$ and the possibility of charring. The reaction was allowed to continue up to 72 hours. Polyanhydroaspartic acid molecules of approximately 2500 daltons (determined by gel permeation) were produced. They were purified by dissolving at pH 8 in water followed by dialysis to remove unreacted aspartic acid although the bulk product is also usable without further purification.

High Temperature Synthesis of Polyaspartate:

L-aspartic acid (500 g) was placed in a Pyrex baking dish and heated at 240° C. in a muffle oven for up to 8 hours, preferably 6 hours. This resulted in nearly 100% of the aspartic acid being polymerized and no further purification was necessary. Polyanhydroaspartic acid molecules of approximately 6000 daltons (determined by gel permeation) were produced. This molecule itself unexpectedly showed greatly increased activity over the low temperature thermal polyaspartate as an inhibitor of mineral formation.

SYNTHESIS EXAMPLE OF PREFERRED SAMPLE

Example 1

Polyanhydroaspartic acid (9.7 g, 0.1 mole) was hydrolyzed to polyaspartic acid by suspension at pH 10, heated to 60° C. for 1 hour and then neutralized with 10N HCl. Small amounts of 10N NaOH were added during the hour to maintain the pH at 10. L-serine (2.62 g, 0.025 mole) and L-aspartic acid (6.65 g, 0.05 mole) were then added. The resulting solution was dried in the reaction vessel at 120° C. for up to 1 hour under nitrogen. This was necessary in that water prevents peptide bond formation. The temperature was brought up to 155° C. ($\pm 2°$ C.). This reaction was allowed to proceed for up to 24 hours, most preferably 8 to 10 hours. Longer reaction times resulted in near total decomposition of serine. The molar ratio of amino acids mixed for the reaction was preferably 4:2:1, polyaspartate: aspartate: serine. The beginning polyanhydro aspartic acid was most preferably the high temperature form. The product consisted of 1 to 10 serine residues, most preferably 4 to 7. Derivatives of serine, such as alanine and dehydroalanine, are also present in amounts ranging from 1 to 10 residues.

Example 2

Orthophosphoric acid (Fox, S. W. and K. Harada (1960). Thermal copolymerization of amino acids common to protein. *J. Am. Chem. Soc.*, 87, 3745-3751) has been found to be an effective solvent in the thermal synthesis of polyamino acids. It may act as a dehydrating agent or as an acid catalyst. It may also function by producing phosphorylamino acid intermediates, which are mixed acid anhydrides (Fox, S. W. and K. Harada (1958). Thermal copolymerization of amino acids to a product resembling protein. *Science*, 128, 1214).

Polyanhydroaspartic (9.7 g) acid was converted to polyaspartate and neutralized as above. This solution of polyaspartate was dried as above and L-serine (2.62 g), L-aspartic acid (6.65 g), and 10 ml phosphoric acid ($H_3PO_4$, 85 wt %) were added and the temperature was brought up to 155° C. ($\pm 2°$ C.). This reaction was allowed to proceed for up to 10 hours, preferably 6 hours. The molar ratio of polyaspartate: aspartate: serine was 4:2:1 and the moles of $H_3PO_4$ added were from 0.01 to 0.1 preferably 0.02 to 0.04. Phosphoric acid destroys most of the serine so that the final product had less than 1 serine residue/molecule but conversion products of between 1 and 10 alanine residues and 1 to 10 dehydroalanine. The polypeptide showed surprising activity, significantly increased relative to polyaspartate, especially in the inhibition of calcium phosphate formation.

Example 3

L-aspartic acid (13.34 g, 0.1 mole) and L-serine (2.63 g, 0.025 mole) were added to a reaction flask. Phosphoric acid (10 ml, 85 wt %) was added and the reaction was carried out at 155° C. ($\pm 2°$ C.) for up to 10 hours, preferably 6 hours. The molar ratio of aspartate: serine was 4:1 and the moles of $H_3PO_4$ added were from 0.01 to 0.1 preferably 0.02 to 0.04. The final product had no serine, and a mixture of alanine and dehydroalanine similar to the above product.

All thermal copolymers are purified after synthesis by dissolving them in distilled water and dialyzing them against same. These are then lyophilized for storage or, in the case of example 1, chemically phosphorylated as follows.

Serine residues incorporated into thermal polymers were phosphorylated via the method of Neuhaus and Korkes (Neuhaus, F. C. and S. Korkes (1958). Phosphoserine. *Bioch. Prep.*, 6, 75-79) as reported by Sikes et al. (Sikes, C. S. Inhibition of mineral deposition by phosphorylated and related polyanionic peptides. U.S. patent application No. 07/339,672). Phosphorus oxychloride, $POCl_3$, was added as 117 ml (1.25 moles) to 45 ml (2.5 moles) of water. This solution was stirred for one hour, allowing formation of monochlorophosphate ($ClH_2PO_3$). Next, amounts up to 0.25 moles of peptides were added with stirring and occasional heating at 60° C. for two hours. The reaction was ended by dropwise addition of 18 ml (1 mole) of $H_2O$ to degrade any unreacted monochlorophosphate to orthophosphate. Any polyphosphates that may have formed during the reaction were destroyed by addition of 75 ml of 1N HCl and heating in a boiling water bath for at least 10 minutes. Upon cooling, peptides were dialyzed against distilled water followed by lyphilization. The extent of phosphorylation of peptide was monitored spectrophotometrically upon formation of the phosphomolybdate complex (Eisenreich, S. J., R. T. Bannerman, D. E. Armstrong (1975). A simplified phosphorus technique. *Environ. Lett.*, 9, 43-53).

Other useful derivatives are envisioned as well; for example, peptides containing sulfated, phosphonated, and sulfonated residues.

Serine residues incorporated into thermal polymers were sulfated via the pyridinium acetyl sulfate (PAS) method of Penke, et al. (Penke, B., et al. (1984). Synthesis of potent heptapeptide analogues of cholecystokinin.

J. Med. Chem., 27, 845-849) as follows. PAS was prepared by first mixing 28.4 ml of acetic anhydride with 8.05 ml of pyridine at room temperature with constant stirring. This mixture was cooled to −13° C. in an ice-methanol bath. To this solution 5.4 ml of concentrated $H_2SO_4$ were added dropwise. Ether (300 ml) was then added to precipitate the PAS. The precipitate was filtered out and washed with three changes of ether. The remaining PAS was air dried for three hours.

Sulfation was carried out by suspending 100 mg of base hydrolyzed thermal polymer of example 1 in 10 ml of pyridine with stirring. The peptide does not dissolve. To this suspension, 54 mg of PAS were added. This was stirred for 24 hours. The reaction mixture was then diluted with 800 ml of distilled water and the pH adjusted to 7.0 with 4N NaOH. This was purified by filtration followed by 4 washes with methanol. The extent of sulfation was monitored using ion chromatography. A 1 mg/ml solution of sulfated peptide in 0.5 N NaOH was digested by autoclaving for 1 hour at 132° C. and 30 PSI. This stock solution was then diluted to 0.1 mg/ml with deionized water and 100 ml was injected on an Ion Pac AS4A column (Dionex). The sample was eluted at 1 ml/min with a buffer of 1.8M $Na_2CO_3$/1.4M $NaHCO_3$ and conductivity was measured with a Dionex conductivity detector.

Various salts of the peptides may be prepared, such as copper, nickel, aluminum and zinc as well as other metal salts, as the metals themselves are inhibitors of mineral deposition.

Activity Assays:

To measure the ability of the peptides of the present invention to inhibit mineralization, a number of assays have been developed. These assays include the following:

1. pH-drift assay—$CaCO_3$.
2. pH-drift assay calcium phosphate.

The following examples describe how these assays have been employed to measure the ability of the polypeptides to inhibit mineralization.

Example 1: The pH-drift assay—Calcium Carbonate

A solution supersaturated with respect to $CaCO_3$ is prepared by separately pipetting 0.3 ml of 1.0M $CaCl_2$ dihydrate and 0.6 ml of 0.4M $NaHCO_3$ into 29.1 ml of artificial seawater (0.5 NaCl, 0.011M KCl). The reaction vessel is a 50 ml, 3-necked, round-bottom flask partially immersed in a thermostated water bath at 20° C. The reaction vessel is closed to the atmosphere to minimize exchange of $CO_2$. The reaction is started by adjusting the pH upward to 8.3 by titration of μl amounts of 1N NaOH by digital pipette. The initial concentrations are 10 mM of $Ca^{2+}$ and 8 mM dissolved inorganic carbon (DIC). The reaction is monitored by pH electrode and recorded by strip chart.

After a period of stable pH during which crystal nuclei form, the pH begins to drift downward until the reaction ceases due to depletion of reactants and the lowering of pH. The reaction may be quantified by calculations based on DIC equilibria to give the amount of precipitation versus time. In FIG. 1 it can be seen that a change in pH is directly proportional to a change in DIC from pH 8.3 to 7.7, but below 7.7 the buffering effect of the DIC system leads to greater changes in DIC per unit pH.

In all experiments measuring inhibition of $CaCO_3$ crystallization by thermal polypeptides, peptides were added in solution at 0.05 μg/ml. Note that high temperature polyaspartic acid shows increased activity over the low temperature thermal polyaspartate (Table 1, FIG. 1). Also note the dramatic increase in activity after phosphorylation of the thermal PolyAsp:Asp:Ser molecules. The degree of inhibition of $CaCO_3$ formation is indicated by the length of time prior to crystallization, shown by stabilization of pH of the metastable solution at about pH 8.3.

Example 2: The pH-drift assay: Calcium Phosphate

A solution supersaturated with respect to calcium phosphate is prepared by separately pipetting 0.1 ml of 1.32M $CaCl_2$ dihydrate and 0.1 ml of 0.90M $NaH_2PO_4$ into 29.8 ml of distilled water. This yields initial concentrations of 4.4 mM $Ca^{2+}$ and 3.0 mM dissolved inorganic phosphorus (DIP). The reaction vessel is a 50 ml, round-bottom, 3-necked flask partially immersed in a thermostated water bath at 20° C. The reaction vessel is closed to the atmosphere. The reaction begins upon mixing the reactants with an initial pH of 7.4.

Figure 2:
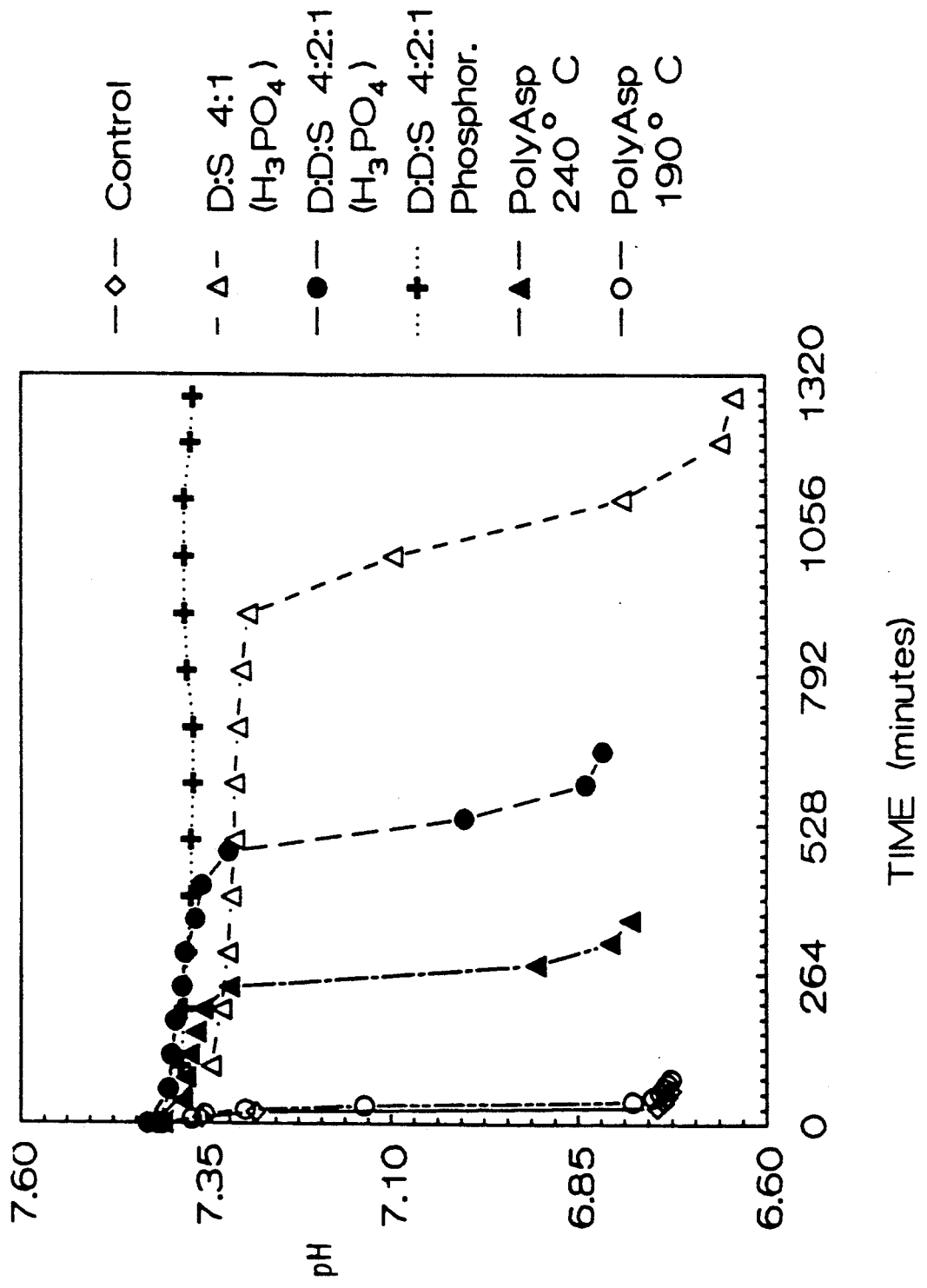
FIG. 2. Calcium phosphate pH-draft assay. Peptide does is 30 µg/ml. D=Asp; S=Ser.

FIG. 2 shows data obtained from this type of assay. Amorphous calcium phosphate (ACP) nucleates immediately and slowly grows as indicated by a slight decrease in pH during the first 30 minutes or so of the assay. Following this, ACP begins to transform to calcium hydroxylapatite (HAP), $Ca_{10}(PO_4)_6(OH)_2$, as indicated by a marked acceleration in the downward pH drift. The reaction ceases as reactants are depleted and the pH is lowered.

In experiments measuring inhibition of calcium phosphate crystallization by thermal polypeptides, the concentration of peptides in solution was 30 μg/ml. The inhibitory activity of the peptides was shown by the degree to which they stabilized the downward pH-drift as calcium phosphate crystals grow. Similar increases in activity to those described for $CaCO_3$ were observed for calcium phosphate inhibition with the phosphorylated peptide clearly showing the best activity (Table 1, FIG. 2).

Uses of the Present Polypeptide

The various polypeptides of this invention may be utilized directly without additives or carriers for inhibiting the deposition of minerals such as phosphates and carbonates whether of inorganic or biological origin. Uses for inhibition of other salts of carbonate, phosphate and sulfate, e.g., magnesium or barium salts, are contemplated. The various polypeptides may be utilized by adding an effective amount of the inhibitor to a liquid in contact with a surface on which the deposits may form. Such is the case of industrially useful and commercially important containers, i.e., boilers, piping, desalinators, cooling towers, and the like. The various amino acid polymers of this invention can be added to water, water-containing liquids or other liquids in an amount as small as 0.01 ng/ml. The upper limit for the amount of the inhibitor is generally only given by its solubility in the liquid to which it is added. However, if the presence of insoluble residues of these polymers does not interfere with industrial operations, it may be desirable to add these inhibitors in an amount greater than that given by their solubility limit.

A preferred range of the various peptide derivatives for controlling inorganic scaling of, e.g., calcium carbonate is $10^{-4}$–$10^2$ μg/ml. Other preferred ranges are $10^{-4}$–0.1 μg/ml and 0.1–$10^2$ μg/ml of the various polymeric derivatives.

When the present inhibitors are utilized for their antifouling characteristics in order to prevent the encrustations of plant or animal organisms, they can be added to a liquid such as water, water-containing liquids or other non-aqueous liquids, preferably in an amount about 0.001–1,000 µg/ml; although larger amounts can also be used. Used within this range of concentrations, the present inhibitors find an application in the prevention of encrustation of organisms in, e.g., running water piping or sewage piping, among others.

The present inhibitors can also be applied directly to a surface before it comes in contact with mineral containing liquids, e.g., industrial containers, marine surfaces such as those in piers, ships, and the like. The present inhibitors may be applied by themselves or in combination with other salt deposition inhibitors, antirust agents, or the like and/or with a carrier, directly to the exposed surface, or they may be mixed with other polymers used for the protection of said surfaces. A variety of carriers are contemplated for the application of the present inhibitors. Some of the most common carriers include aqueous and non-aqueous liquids, gels, oils, organic and inorganic solvents, compressed gases, and the like. However, any carrier may be used according to the needs. When used in high concentrations by themselves, the polyamino acid inhibitors of this invention may be highly viscous and can be easily applied to a surface.

After the application of the inhibitors, an appropriate length of time may be allowed for the penetration of the inhibitor into the surface, as is the case with porous surface materials, such as wood, ceramics, and the like. Thus, a large storage of the present inhibitors is created within the material and the surface may then be partially sealed with a coat-forming polymer to retard release of the active component.

Alternatively, the various polypeptides may be mixed with a carrier to form a suspension which can be applied to a surface. The present inhibitors may be applied to any type of surface which may be exposed to the formation of inorganic or biological mineral deposits. Some of the most common materials to which the present inhibitors may be applied are metals, woods, synthetic polymers and copolymers, glass, ceramics, and painted to otherwise coated surfaces, although other materials are also contemplated. When in contact with the mineral-containing liquid, the inhibitors will slowly leach out from underneath the polymeric coating layer. The present inhibitors may further be applied in a mixture with the coating forming polymer, e.g., paints or any synthetic polymer used for the protection of surfaces such as polyurethanes. Alternatively, the coat-forming material may be an emulsion paint, etc. When the present inhibitors are used in admixtures with a coat-forming polymer or material, they can be used in a concentration of between 0.001–90% by weight of the total composition, although higher or lower concentrations are also contemplated in this invention. Some of the preferred concentrations are 1–75% by weight. Other preferred concentrations are 5–25%, 25–50% and 10–40% by weight. When applied to a surface the present inhibitors may be formulated with a carrier in the form of powder, solution, suspension, gel, oil, aerosol, paste or viscous colloid.

In a preferred embodiment of the present invention, the present materials may serve as inhibitors of dental tartar and plaque formation (referred to herein as tartar barrier agents) for human or animal use. In accordance with this embodiment of the present invention, the oral compositions may comprise any conventional pharmaceutically acceptable oral hygiene formulation that contains and is compatible with an effective amount of an antidental calculus agent as disclosed herein. Such formulations include, for example, mouthwashes, rinses, irrigating solutions, abrasive and non-abrasive gel dentifrices, denture cleansers, coated dental floss and interdental stimulator coatings, chewing gums, lozenges, breath fresheners, foams and sprays. These formulations may be used to treat natural or artificial tooth enamel, or any orally compatible material which is subject to mineral deposition. Although human use is preferred, use in animals is also possible.

The tartar barrier agents may be present in the formulations in effective concentrations generally in the range of from about 0.05 wt. % to as much as 30 wt. % or the limit of compatibility with a vehicle. A preferred concentration range for the agents of the formulations of the invention is from about 0.5 to about 10 wt. %. A more preferred range is from about 2 to about 8 wt. %.

The metal salts of the peptides of the present invention can be included in compositions up to the limit of their solubility therein, preferably around 0.2 to 2%, with 10% being a reasonable maximum limit, by weight. In addition, the peptides of the present invention may be used in their acid forms, or as, for example, sodium salts, alone or in combination along with inorganic salts which are known by the prior art to be inhibitors of mineralization. The combined percentage of these materials, which together operate as anticalculus agents, can be included in the composition in concentrations of from 0.2 to 10%, by weight, preferably around 2% by weight.

The pH of these preparations should be between about pH 5 and 10, preferably between pH 5 and 8, more preferably between about 6 and 7.5. A pH lower than 5 is undesirable because of the possible enhancement of enamel demineralization.

Suitable conventional pharmaceutically acceptable vehicles that can be employed with the tartar barrier agents to prepare the compositions of this invention may comprise water, ethanol; such humectants as polypropylene glycol, glycerol and sorbitol; such gelling agents as cellulose derivatives, for example, Methocel carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidal magnesium aluminosilicate complexes such as Veegum, and mucoprotein thickening agents such as Carbopol 934; gel stabilizers such as the silicon dioxides, for example Cab-O-Sil M5, and polyvinyl-pyrrolidone; sweeteners such as sodium saccharin and aspartame; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the tartar barrier agent compositions of this invention.

EXAMPLE A

Mouthwash Solution

| | |
|---|---|
| Tartar barrier agent | 0.5–2.0% w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B

Mouthwash Solution

| | |
|---|---|
| Tartar barrier agent | 0.5–3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C

Abrasive Dentifrice Gel

| | |
|---|---|
| Tartar barrier agent | 2.0–10.0% w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D

Chewing Gum

| | |
|---|---|
| Tartar barrier agent | 1.0–11.0% w/w |
| Gum Base | 21.3 |
| Sugar | 48.5–58.5 |
| Corn Syrup (Baume 45) | 18.2 |
| Flavors | 1.0 |
| | 100.0 |

EXAMPLE E

Nonabrasive Gel Dentifrice

| | |
|---|---|
| Tartar barrier agent | 0.05–30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium saccharin | 0.2 |
| Flavors | 1.5 |
| | 100.0 |

In addition to the above materials which can be included in the present tartar barrier compositions, it is also contemplated to include therein a protease inhibitor to prevent the present peptides and polypeptides from being degraded by various proteolytic enzymes.

Examples of such inhibitors include aprotinin and trypsin inhibitor types I-P, I-S, II-L, II-O, II-S, IIT, III-O, and IV-O, although other inhibitors are within the scope of this invention. Similarly, when phosphopeptides are employed, it is contemplated to use phosphatase inhibitors in conjunction with the polypeptide to prevent or inhibit dephosphorylation of the polypeptides. Examples of such phosphatase inhibitors are sodium fluoride, adenosine diphosphate, and vinyl ether/maleic acid polymers (gantrez). Use of other phosphatase inhibitors is also possible.

The present peptides and polypeptides could also be linked to antibodies, or otherwise used in combination with antimicrobial agents, particularly those against cavity-causing bacteria, as part of a tartar barrier composition to enhance antibacterial activity.

The polypeptides of the present invention may also find suitable use in treatment and prevention of mineral buildups in arteries and veins, such as in atherosclerosis.

In this connection, the mode of administration of the polypeptides is preferably parenteral, i.e., intravenous, intraperitoneal, intramuscular, or subcutaneous, with intravenous administration being most preferred. They may be administered alone, without a carrier vehicle; however, they may also be administered with pharmaceutically acceptable nontoxic carriers, the proportions of which are determined by the suitability and chemical nature of the particular carrier. For intravenous or intramuscular administration, they may be used in the form of a sterile solution containing other solutes, for example, sufficient saline or glucose to make the solution isotonic. Like insulin, the peptides of the subject invention may also prove to be administrable by use of a continuous perfusion device, which should simplify the method of administration.

The physician will determine the dosage which will be most suitable for a particular situation. Dosages will generally depend upon the age and size of the patient, and the seriousness of the condition to be treated. A normal dosage will generally be in the range of 200–600 mg peptide per day.

The polypeptides of the present invention can also be used to impregnate prosthetic devices. For example, the polypeptides of the present invention could be incorporated into polymeric based (e.g., a copolymer of ethylene - vinyl acetate or a silicon rubber) controlled released drug delivery matrices for site specific therapy directly into the perianular region of the heart prosthesis (Levy, R. J. et al., CRC Critical Reviews in Biocompatibility 2, 148–187 (1986)). Controlled release devices incorporating a phosphonate derivative have been formulated to deliver that drug for more than 30 years without depletion. In addition, valve cusps could also be preloaded with a polypeptide according to the present invention via covalent aldehyde-amino linkages; such an approach could be useful as a primary anti-calcium measure or as an adjunct for priming controlled release anti-mineralization therapy.

The invention now being fully described, it will be apparent to one of ordinary skill in the art that many changes and modifications can be made thereto, without departing from the spirit or scope of the invention as set forth therein.

| Reactants | Temp of Synthesis | Time of Synthesis | Amino Acid Analysis of Product Composition Exclusive of Asp | Inhibition $CaCO_3/CaPO_4$ minutes | Approx. M.W. (GPC) |
|---|---|---|---|---|---|
| PolyAsp | 190° C. | 72 hr | | 120/50 | 2000 |
| | 240° C. | 6 hr | | 220/240 | 6000** |
| | | 8 hr | | 230/279 | 6000** |
| Asp:Ser (4:1) | 155° C. | 12 hr | 2.4% Ser/2.5% Ala; d-Ala* | /95 | 1100 |
| | | 18 hr | 6.6% Ser/5.5% Ala; d-Ala | /94 | 1100 |
| | | 24 hr | 5.2% Ser/3.4% Ala; d-Ala | /250 | 1100 |
| | | 30 hr | 7.2% Ser/3.8% Ala; d-Ala | /410 | 1100 |
| | | 36 hr | 0.2% Ser/0.5% Ala; d-Ala | /65 | 1100 |
| | | 48 hr | 0.3% Ser/1.1% Ala; d-Ala | /75 | 1100 |
| Asp:Ser (4:1) $H_3PO_4$ | 155° C. | 6 hr | 9.2% Ala; d-Ala | 520/760 | 2400 |
| PolyAsp:Asp:PSer $H_3PO_4$ | 155° C. | 6 hr | 0.5% Ser/10% Ala; d-Ala | 540/503 | 2200 |
| PolyAsp:Asp:PSer (4:2:1) low-temp PolyAsp | 155° C. | 9.5 hr | 8.3% Ser/d-Ala present | 790/1115 | 2500 |
| PolyAsp:Asp:PSer (4:2:1) hi-temp PolyAsp | 155° C. | 9 hr | 8.8% Ser/3.1% d-Ala | 726/1240 | 2800 |
| | | 18 hr | 6.1% Ser/d-Ala present | 393/810 | 2500 |
| PolyAsp:Asp:Ser (4:2:1) | | 24 hr | 6.7% Ser/d-Ala present | /390 | 2500 |

*d-Ala = dehydroalanine
** - Highly branched molecules. The apparent molecular weight may differ from actual, due to interference with the GPC system induced by branching. The system is calibrated for linear polyaspartates

What is claimed is:

1. A method for the synthesis of a polypeptide, comprising combining an amino acid, X, selected from the group consisting of aspartate, glutamate, glutamine, asparagine, polyaspartic acid, and mixtures thereof, together with serine, in a reaction vessel, and heating said reaction vessel to a temperature sufficient to cause polymerization of said amino acids and below the decomposition temperature of serine, for up to 72 hours.

2. The method of claim 1, wherein said heating is conducted at 120° C.-170° C.

3. The method of claim 1, wherein said method comprises eliminating oxygen from said reaction vessel, to preclude charring.

4. The method of claim 3, wherein said oxygen is eliminated by continuous purging of the reaction vessel with nitrogen.

5. The method of claim 3, wherein X comprises polyaspartate.

6. The method of claim 5, wherein said polyaspartate is synthesized by heating aspartic acid in a reaction vessel maintained in a heating medium at about 160°-190° C. for a period of up to 72 hours until polymerization of said aspartic acid occurs.

7. The method of claim 6, wherein oxygen is eliminated from said reaction vessel, to preclude charring.

8. The method of claim 7, wherein oxygen is eliminated by continuous purging of the reaction vessel with a stream of nitrogen.

9. The method of claim 5, wherein polyaspartate is synthesized by placing aspartic acid in an open reaction vessel and heating at a temperature of about 190°-260° C. for a period of up to 8 hours until said aspartic acid polymerizes.

10. The method of claim 11, further comprising adding phosphoric acid to said reaction vessel prior to polymerization.

11. The method of claim 1, further comprising derivitizing serine residues in said polypeptide after said polymerization, comprising phosphorylating, sulfating, phosphonating or sulfonating said serine residues.

12. A method of inhibiting mineral deposition on a surface, comprising contacting said surface with a liquid, said liquid comprising a polypeptide in a concentration no less than 0.01 ng/ml, wherein said polypeptide is produced by a process comprising combining an amino acid, X, selected from the group consisting of aspartate, glutamate, glutamine, asparagine, polyaspartic acid, and mixtures thereof, together with serine, in a reaction vessel, and heating said reaction vessel to a temperature sufficient to cause polymerization of said amino acid and below the decomposition temperature of serine, for up to 72 hours, to yield said polypeptide.

13. The method of claim 12, wherein said concentration of said polypeptide is $10^{-4}$ to $10^2$ μg/ml.

14. A method of inhibiting the formation of dental tartar and plaque in animals comprising treating surfaces susceptible to said tartar and plaque formation with an oral composition comprising an effective amount of a polypeptide in a pharmaceutically acceptable carrier, wherein said polypeptide is produced by a process comprising combining an amino acid, X, selected from the group consisting of aspartate, glutamate, glutamine, asparagine, polyaspartic acid, and mixtures thereof, together with serine, in a reaction vessel, and heating said reaction vessel to a temperature sufficient to cause polymerization of said amino acid and below the decomposition temperature of serine, for up to 72 hours, to yield said polypeptide.

15. The method of claim 14, wherein said polypeptide is present in an amount of 0.05 wt. % to 30 wt. % of the total oral composition.

* * * * *